United States Patent
Gaynor

(10) Patent No.: US 10,383,322 B2
(45) Date of Patent: Aug. 20, 2019

(54) FISHING AND SAILING ACTIVITY DETECTION

(71) Applicant: Navico Holding AS, Egersund (NO)

(72) Inventor: Phillip King Gaynor, Chesapeake, VA (US)

(73) Assignee: NAVICO HOLDING AS, Egersund (NO)

(*) Notice: Subject to any disclaimer, the term of this patent is extended or adjusted under 35 U.S.C. 154(b) by 1148 days.

(21) Appl. No.: 14/195,610

(22) Filed: Mar. 3, 2014

(65) Prior Publication Data
US 2015/0057965 A1 Feb. 26, 2015

Related U.S. Application Data

(60) Provisional application No. 61/868,444, filed on Aug. 21, 2013.

(51) Int. Cl.
*A61B 5/11* (2006.01)
*G01S 7/00* (2006.01)
(Continued)

(52) U.S. Cl.
CPC .............. *A01K 97/00* (2013.01); *A01K 79/00* (2013.01); *A01K 99/00* (2013.01); *A61B 5/1118* (2013.01);
(Continued)

(58) Field of Classification Search
CPC .... A01K 91/18; A61K 97/00; A61K 47/4865; A61K 47/48653; A61K 31/355;
(Continued)

(56) References Cited

U.S. PATENT DOCUMENTS 4,751,787 A * 6/1988 Jonsson ................ A01K 91/18
43/27.4
4,829,493 A 5/1989 Bailey
(Continued)

FOREIGN PATENT DOCUMENTS

| DE | 102004059619 A1 | 6/2006 |
|---|---|---|
| EP | 749687 A1 | 12/1996 |
| EP | 1 561 377 A1 | 8/2005 |
| EP | 1782687 | 5/2007 |
| EP | 2356902 A1 | 8/2011 |
| EP | 2 613 223 A1 | 7/2013 |

(Continued)

OTHER PUBLICATIONS

Office Action Issued in Canadian Patent Application 2,921,317, dated Feb. 7, 2017.
(Continued)

*Primary Examiner* — Regis J Betsch
*Assistant Examiner* — Kaleria Knox
(74) *Attorney, Agent, or Firm* — Nelson Mullins Riley & Scarborough LLP

(57) ABSTRACT

Various implementations described herein are directed to a wearable device used to determine whether motion data and heart rate data correspond to a fishing activity. The wearable device may include a heart rate sensor and a motion sensor. The wearable device may include a computer system with a processor and memory. The memory may have a plurality of executable instructions. When the executable instructions are executed by the processor, the processor may receive motion data from the motion sensor, receive heart rate data from the heart rate sensor, and determine whether the received motion data and heart rate data corresponds to a fishing activity.

18 Claims, 6 Drawing Sheets

(51) Int. Cl.

| | | |
|---|---|---|
| G06F 3/01 | (2006.01) | |
| G06K 9/00 | (2006.01) | |
| G06T 7/60 | (2017.01) | |
| H04N 5/91 | (2006.01) | |
| H04Q 9/00 | (2006.01) | |
| A01K 79/00 | (2006.01) | |
| A01K 97/00 | (2006.01) | |
| A01K 99/00 | (2006.01) | |
| B63B 49/00 | (2006.01) | |
| G01B 21/00 | (2006.01) | |
| G01C 21/20 | (2006.01) | |
| G01S 15/96 | (2006.01) | |
| G06F 11/30 | (2006.01) | |
| G06F 11/34 | (2006.01) | |
| G06F 15/02 | (2006.01) | |
| G06F 3/023 | (2006.01) | |
| G06Q 10/00 | (2012.01) | |
| G06Q 50/00 | (2012.01) | |
| H04N 5/232 | (2006.01) | |
| H04N 21/4335 | (2011.01) | |
| G06F 16/9535 | (2019.01) | |
| G08C 17/02 | (2006.01) | |
| G06T 11/20 | (2006.01) | |
| G11B 27/031 | (2006.01) | |
| G11B 27/17 | (2006.01) | |
| G11B 31/00 | (2006.01) | |
| G11B 27/28 | (2006.01) | |
| G11B 27/34 | (2006.01) | |
| G06F 3/0346 | (2013.01) | |
| G06T 7/246 | (2017.01) | |
| G06T 7/292 | (2017.01) | |

(52) U.S. Cl.
CPC ............ *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 16/9535* (2019.01); *G06K 9/00342* (2013.01); *G06Q 10/00* (2013.01); *G06Q 50/01* (2013.01); *G06T 7/246* (2017.01); *G06T 7/292* (2017.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/232* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02D 10/34* (2018.01)

(58) Field of Classification Search
CPC .. G06F 19/3481; G06F 19/3418; A63F 13/06; A63F 13/216; A63B 24/0062; A63B 24/00; A61B 5/0422; A61B 5/11; A61B 5/02405; A61B 5/222; A61B 5/02444; A61B 5/02427

USPC .............. 43/27.4; 424/131.1, 770; 702/187; 463/43, 7; 434/247; 607/4; 377/23; 600/301; 340/539.12
See application file for complete search history.

(56) References Cited

U.S. PATENT DOCUMENTS

| | | |
|---|---|---|
| 4,879,697 A | 11/1989 | Lowrance et al. |
| 5,025,423 A | 6/1991 | Earp |
| 5,191,341 A | 3/1993 | Gouard et al. |
| 5,228,228 A | 7/1993 | Meissner |
| 5,321,391 A | 6/1994 | Fox |
| 5,446,775 A * | 8/1995 | Wright ............... A61B 5/11 377/23 |
| 5,537,380 A | 7/1996 | Sprankle, Jr. et al. |
| 5,546,695 A | 8/1996 | Langer |
| 6,045,076 A | 4/2000 | Daniels |
| 6,125,571 A | 10/2000 | Sigwald |
| 6,222,449 B1 | 4/2001 | Twining |
| 6,225,984 B1 | 5/2001 | Crawford |
| 6,252,544 B1 | 6/2001 | Hoffberg |
| 6,263,147 B1 | 7/2001 | Tognazzini |
| 6,321,158 B1 | 11/2001 | DeLorme et al. |
| 6,411,283 B1 | 6/2002 | Murphy |
| 6,418,080 B2 | 7/2002 | Inouchi |
| 6,421,299 B1 | 7/2002 | Betts et al. |
| 6,459,372 B1 | 10/2002 | Branham et al. |
| 6,567,792 B1 | 5/2003 | Arnold |
| 6,584,722 B1 | 7/2003 | Walls |
| 6,587,740 B2 | 7/2003 | Byrne et al. |
| 6,751,626 B2 | 6/2004 | Brown et al. |
| 6,761,692 B2 | 7/2004 | Angelsen et al. |
| 6,798,378 B1 | 9/2004 | Walters |
| 6,816,782 B1 | 11/2004 | Walters et al. |
| 7,002,579 B2 | 2/2006 | Olson |
| 7,236,426 B2 | 6/2007 | Turner et al. |
| 7,243,457 B1 | 7/2007 | Smith et al. |
| 7,319,992 B2 | 1/2008 | Gaos |
| 7,321,824 B1 | 1/2008 | Nesbitt |
| 7,430,461 B1 | 9/2008 | Michaels |
| 7,652,952 B2 | 1/2010 | Betts et al. |
| 7,669,360 B2 | 3/2010 | Davidson |
| 7,710,825 B2 | 5/2010 | Betts et al. |
| 7,722,218 B2 | 5/2010 | Leung |
| 7,729,203 B2 | 6/2010 | Betts et al. |
| 7,755,974 B2 | 7/2010 | Betts et al. |
| 7,812,667 B2 | 10/2010 | Fagg |
| 7,870,496 B1 | 1/2011 | Sherwani |
| 7,890,867 B1 | 2/2011 | Margulis |
| 8,019,532 B2 | 9/2011 | Sheha et al. |
| 8,040,758 B1 | 10/2011 | Dickinson |
| 8,063,540 B2 | 11/2011 | Angelsen et al. |
| 8,082,100 B2 | 12/2011 | Grace et al. |
| 8,364,806 B2 | 1/2013 | Short et al. |
| 8,452,797 B1 | 5/2013 | Paleja et al. |
| 8,468,164 B1 | 6/2013 | Paleja et al. |
| 8,512,238 B2 * | 8/2013 | Nissila ............... A61B 5/222 128/903 |
| 8,721,453 B2 * | 5/2014 | Rosing ............... A63F 13/216 463/1 |
| 9,439,411 B2 | 9/2016 | Bailey |
| 9,507,562 B2 | 11/2016 | Bailey |
| 9,572,335 B2 | 2/2017 | Bailey |
| 9,615,562 B2 | 4/2017 | Bailey |
| 2001/0054961 A1 | 12/2001 | Twining |
| 2002/0035574 A1 | 3/2002 | Dumas |
| 2002/0093541 A1 | 7/2002 | Schileru-Key |
| 2002/0099457 A1 | 7/2002 | Fredlund et al. |
| 2002/0116421 A1 | 8/2002 | Fox et al. |
| 2003/0046689 A1 | 3/2003 | Gaos |
| 2003/0056419 A1 | 3/2003 | Squires et al. |
| 2003/0089020 A1 | 5/2003 | Dirito |
| 2003/0147981 A1 * | 8/2003 | Gillam ............... A61K 31/355 424/770 |
| 2004/0124297 A1 | 7/2004 | Steer |
| 2004/0162830 A1 | 8/2004 | Shirwadkar et al. |

(56) References Cited

U.S. PATENT DOCUMENTS

| | | |
|---|---|---|
| 2004/0193364 A1 | 9/2004 | Chojnacki |
| 2004/0198554 A1* | 10/2004 | Orr ................. A63B 24/00 482/8 |
| 2004/0249860 A1 | 12/2004 | Stechschulte et al. |
| 2005/0011105 A1 | 1/2005 | Cameron et al. |
| 2005/0037872 A1 | 2/2005 | Fredlund et al. |
| 2005/0102101 A1 | 5/2005 | Beesley et al. |
| 2006/0013066 A1 | 1/2006 | Nishimori et al. |
| 2006/0048434 A1 | 3/2006 | Congel |
| 2006/0053028 A1 | 3/2006 | Congel |
| 2006/0119585 A1 | 6/2006 | Skinner |
| 2006/0224940 A1 | 10/2006 | Lee |
| 2006/0265931 A1 | 11/2006 | McFadden et al. |
| 2007/0011334 A1 | 1/2007 | Higgins et al. |
| 2007/0045010 A1 | 3/2007 | Kasperek |
| 2007/0058489 A1 | 3/2007 | Bratcher |
| 2007/0220798 A1 | 9/2007 | Davidson |
| 2008/0032666 A1 | 2/2008 | Hughes et al. |
| 2008/0126935 A1 | 5/2008 | Blomgren |
| 2008/0165022 A1 | 7/2008 | Herz et al. |
| 2008/0204424 A1 | 8/2008 | Jin et al. |
| 2008/0246627 A1 | 10/2008 | Guazzelli |
| 2009/0064055 A1 | 3/2009 | Chaudhri et al. |
| 2009/0099871 A1 | 4/2009 | Gadodia |
| 2009/0105952 A1 | 4/2009 | Grace et al. |
| 2009/0179789 A1 | 7/2009 | Haughay, Jr. et al. |
| 2009/0231190 A1 | 9/2009 | Grumbles |
| 2009/0240354 A1 | 9/2009 | Davidson |
| 2009/0241636 A1 | 10/2009 | Obori |
| 2009/0249247 A1 | 10/2009 | Tseng et al. |
| 2009/0258710 A1* | 10/2009 | Quatrochi .......... A63B 24/0062 463/43 |
| 2009/0271054 A1 | 10/2009 | Dokken |
| 2009/0287409 A1 | 11/2009 | Summers |
| 2009/0293336 A1 | 12/2009 | Lankinen |
| 2009/0295626 A1 | 12/2009 | Su |
| 2010/0049468 A1 | 2/2010 | Papadourakis |
| 2010/0080082 A1 | 4/2010 | Betts et al. |
| 2010/0121716 A1* | 5/2010 | Golan .................. G01S 5/0027 705/14.58 |
| 2010/0145601 A1 | 6/2010 | Kurtti et al. |
| 2010/0198650 A1 | 8/2010 | Shaw |
| 2010/0199225 A1 | 8/2010 | Coleman et al. |
| 2010/0226203 A1 | 9/2010 | Buttle et al. |
| 2010/0250122 A1 | 9/2010 | Kubota et al. |
| 2010/0295781 A1 | 11/2010 | Alameh et al. |
| 2010/0319235 A1 | 12/2010 | Panaro |
| 2011/0007035 A1 | 1/2011 | Shai |
| 2011/0013484 A1 | 1/2011 | Coleman et al. |
| 2011/0013485 A1 | 1/2011 | Maguire |
| 2011/0019887 A1 | 1/2011 | Roehrig et al. |
| 2011/0025720 A1 | 2/2011 | Jo et al. |
| 2011/0067290 A1 | 3/2011 | Miskatovic |
| 2011/0082644 A1 | 4/2011 | Imasaka et al. |
| 2011/0154183 A1 | 6/2011 | Burns et al. |
| 2011/0208479 A1* | 8/2011 | Chaves ................. A01K 97/00 702/187 |
| 2011/0213515 A1 | 9/2011 | Haymart et al. |
| 2011/0214500 A1 | 9/2011 | Cabrera et al. |
| 2011/0257819 A1 | 10/2011 | Chen et al. |
| 2012/0001773 A1 | 1/2012 | Lyons et al. |
| 2012/0010478 A1* | 1/2012 | Kinnunen .......... A61B 5/02405 600/301 |
| 2012/0011437 A1 | 1/2012 | James et al. |
| 2012/0014220 A1 | 1/2012 | DePasqua |
| 2012/0047790 A1 | 3/2012 | Hess et al. |
| 2012/0069712 A1 | 3/2012 | Potanin et al. |
| 2012/0095978 A1 | 4/2012 | Levin et al. |
| 2012/0106300 A1 | 5/2012 | Maguire |
| 2012/0144384 A1 | 6/2012 | Baek |
| 2012/0144723 A1 | 6/2012 | Davidson |
| 2012/0185801 A1 | 7/2012 | Madonna et al. |
| 2012/0253485 A1 | 10/2012 | Weast et al. |
| 2012/0293323 A1* | 11/2012 | Kaib .................. G06F 19/3418 340/539.12 |
| 2012/0316456 A1 | 12/2012 | Rahman et al. |
| 2012/0316458 A1 | 12/2012 | Rahman et al. |
| 2012/0317167 A1 | 12/2012 | Rahman et al. |
| 2013/0007665 A1 | 1/2013 | Chaudhri et al. |
| 2013/0040714 A1* | 2/2013 | Rosing ................ A63F 13/216 463/7 |
| 2013/0074051 A1 | 3/2013 | Freeman |
| 2013/0096575 A1 | 4/2013 | Olson |
| 2013/0107031 A1 | 5/2013 | Atkinson |
| 2013/0109997 A1* | 5/2013 | Linke ................. G06F 19/3418 600/549 |
| 2013/0271301 A1 | 10/2013 | Kabel et al. |
| 2013/0281087 A1 | 10/2013 | Ruhanen et al. |
| 2013/0307720 A1 | 11/2013 | Lilburn |
| 2013/0343151 A1 | 12/2013 | Shiraki et al. |
| 2014/0012587 A1 | 1/2014 | Park |
| 2014/0032468 A1 | 1/2014 | Anandaraj |
| 2014/0071059 A1 | 3/2014 | Girault |
| 2014/0111368 A1 | 4/2014 | Lee et al. |
| 2014/0135592 A1* | 5/2014 | Ohnemus ............ A61B 5/7275 600/301 |
| 2014/0135631 A1* | 5/2014 | Brumback .......... A61B 5/02438 600/479 |
| 2014/0164375 A1 | 6/2014 | Persson et al. |
| 2014/0180566 A1 | 6/2014 | Malhotra |
| 2014/0195297 A1 | 7/2014 | Abuelsaad et al. |
| 2014/0221854 A1* | 8/2014 | Wai .................... A61B 5/02444 600/508 |
| 2014/0358483 A1 | 12/2014 | da Rosa |
| 2015/0019135 A1 | 1/2015 | Kacyvenski |
| 2015/0051786 A1 | 2/2015 | Wang |
| 2015/0054655 A1 | 2/2015 | Bailey |
| 2015/0054732 A1 | 2/2015 | Bailey |
| 2015/0054828 A1 | 2/2015 | Bailey |
| 2015/0054829 A1 | 2/2015 | Bailey |
| 2015/0055827 A1 | 2/2015 | Bailey |
| 2015/0055930 A1 | 2/2015 | Bailey |
| 2015/0057929 A1 | 2/2015 | Bailey |
| 2015/0057965 A1 | 2/2015 | Gaynor |
| 2015/0057968 A1 | 2/2015 | Bailey |
| 2015/0058020 A1 | 2/2015 | Bailey |
| 2015/0058237 A1 | 2/2015 | Bailey |
| 2015/0058323 A1 | 2/2015 | Bailey |
| 2015/0245777 A1* | 9/2015 | Della Torre ............ A61B 5/11 600/301 |
| 2015/0310524 A1 | 10/2015 | Gospodarek et al. |
| 2015/0313199 A1 | 11/2015 | Castaneda et al. |
| 2015/0342481 A1* | 12/2015 | Liu ................... A61B 5/02427 600/479 |
| 2016/0125348 A1 | 5/2016 | Dyer et al. |

FOREIGN PATENT DOCUMENTS

| | | |
|---|---|---|
| GB | 2244195 A | 11/1991 |
| GB | 2426680 A | 12/2006 |
| GB | 2470904 | 12/2010 |
| JP | 2004 207812 A | 7/2004 |
| JP | 2006-158239 A | 6/2006 |
| JP | 2010 193284 A | 9/2010 |
| JP | 2011 139647 A | 7/2011 |
| WO | 1998/02037 A1 | 1/1998 |
| WO | 2004/088572 | 10/2004 |
| WO | 2010/056392 | 5/2010 |
| WO | WO 2012/059734 A1 | 5/2012 |
| WO | 2012/170163 | 12/2012 |
| WO | 2014/088508 A1 | 6/2014 |
| ZA | 200 308 052 A | 7/2004 |

OTHER PUBLICATIONS

Allen, et al.; Upper Extremity Kinematic Trends of Fly-Casting; Establishing the Effects of Line Length; Sports Biomechanics; vol. 7, No. 1; Jan. 1, 2008; pp. 38-53.

(56) References Cited

OTHER PUBLICATIONS

First look at new Mio Link ANT +/Bluetooth Smart optical heart rate wrist band; http://www.dcrainmaker.com/2014/01/mio-link-first-look.html; Jan. 6, 2014 (accessed Apr. 18, 2016).
SAS, "SAS BI Dashboard 4.31 User's Guide", Second Edition, by SAS Electronic book, Aug. 1, 2012, downloaded at http://support.sas.com/documentation/cdl/en/bidbrdug/65580/PDF/default/bidrdrug.pdf.
PCT International Search Report and Written Opinion; PCT/IB2014/063974, dated Dec. 2, 2014; all enclosed pages cited.
PCT International Search Report and Written Opinion; PCT/IB2014/063975, dated Dec. 3, 2014; all enclosed pages cited.
PCT International Search Report and Written Opinion; PCT/IB2014/063976, dated Dec. 12, 2014; all enclosed pages cited.
PCT International Search Report and Written Opinion; PCT/IB2014/063979, dated Jan. 7, 2015; all enclosed pages cited.
PCT International Search Report and Written Opinion; PCT/IB2014/063980, dated Jan. 5, 2015; all enclosed pages cited.
PCT International Search Report and Written Opinion; PCT/IB2014/063982, dated Dec. 22, 2014; all enclosed pages cited.
PCT International Search Report and Written Opinion; PCT/IB2014/063983, dated Mar. 5, 2015; all enclosed pages cited.
PCT International Search Report and Written Opinion; PCT/IB2014/063973, dated Nov. 28, 2014; all enclosed pages cited.
PCT International Search Report and Written Opinion; PCT/IB2014/063981, dated Feb. 10, 2015; all enclosed pages cited.
PCT International Search Report and Written Opinion; PCT/IB2014/063978, dated Dec. 19, 2014; all enclosed pages cited.
PCT International Search Report and Written Opinion; PCT/IB2014/063977, dated Nov. 28, 2014; all enclosed pages cited.
First look at new Mio Link ANT+/Bluetooth Smart optical heart rate wrist band; http://www.dcrainmaker.com/2014/01/mio-link-first-look.html; Jan. 6, 2014 (accessed Mar. 3, 2014).
PCT International Search Report and Written Opinion; PCT/IB2013/060285; dated Feb. 18, 2014.
PCT International Search Report and Written Opinion; PCT/US2013/048177; dated Oct. 21, 2013.
PCT International Search Report and Written Opinion; PCT/US2013/047869; dated Oct. 21, 2013.
PCT International Search Report and Written Opinion; PCT/US2013/048129; dated Oct. 17, 2013.
PCT International Search Report and Written Opinion; PCT/US2013/047926; dated Oct. 11, 2013.
PCT International Search Report and Written Opinion; PCT/US2013/047645; dated Sep. 27, 2013.
McElderry; At-Sea Observing Using Video-Based Electronic Monitoring; Prepared for: Electronic Monitoring Workshop Jul. 29-30, 2008; Archipelago Marine Research Ltd.
Cristando et al. "Nikeplus Ecosystem Strategy" retreived Sep. 1, 2017 from <http://studylib.net/doc/8718940/nikeplus-ecosystem-strategy> 12 pages.
Joey Davidson, "Jaybird Reign REVIEW—Lightweight, simple, lacking" Feb. 28, 2016, Technobuffalo, retrieved Sep. 1, 2017 from <https://www.technobuffalo.com/reviews/jaybird-reign-review/> 14 pages.

* cited by examiner

FISHING AND SAILING ACTIVITY DETECTION

CROSS-REFERENCE TO RELATED APPLICATIONS

This application claims the benefit of U.S. Provisional Patent Application Ser. No. 61/868,444, filed Aug. 21, 2013 titled FISHING DATA COLLECTION AND USE, and the disclosure of which is incorporated herein by reference.

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Accurate data, including, for example, a count of fishing casts made, can be very useful for a fisherman. A device that can capture this data can provide advantages to a fisherman. Such advantages include requiring less time to record information, and collecting more accurate data.

SUMMARY

Described herein are implementations of various technologies for an apparatus for determining whether motion and heart rate data correspond to a fishing activity. The apparatus is a wearable device. The wearable device includes a heart rate sensor and a motion sensor. The wearable device includes a computer system with a processor and memory. The memory has a plurality of executable instructions. In one implementation, when the executable instructions are executed by the processor, the processor may receive motion data from the motion sensor, receive heart rate data from the heart rate sensor, and determine whether the received motion and heart rate data corresponds to a fishing activity.

Described herein are also implementations of various technologies for a method for determining whether motion data and heart rate data correspond to a fishing activity. In one implementation, a non-transitory computer-readable medium having stored thereon computer-executable instructions which, when executed by a computer, cause the computer to perform various actions. The actions may include receiving motion data from a first sensor and heart rate data from a second sensor. The received motion data and heart rate data may be analyzed to determine whether the received data corresponds to a fishing activity.

Described herein are also implementations of various technologies for an apparatus for determining a level of physical exertion. The apparatus is a wearable device. The wearable device includes a motion sensor and a heart rate sensor. The wearable device includes a computer system with a processor and memory. The memory has a plurality of executable instructions. In one implementation, when the executable instructions are executed by the processor, the processor may receive motion data from the motion sensor, receive heart rate data from the heart rate sensor, and determine a level of physical exertion based on the motion data and the heart rate data. The level of physical exertion may correspond to an activity during fishing or sailing.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

DETAILED DESCRIPTION

Figure 1:
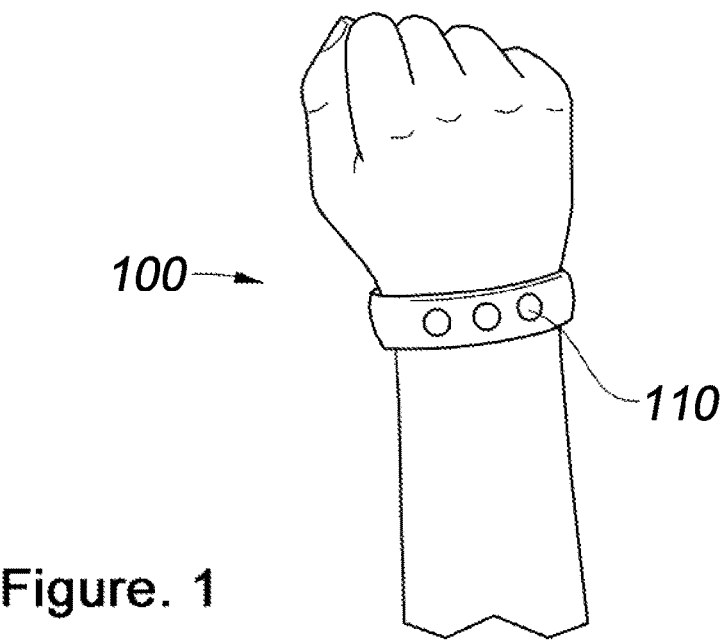
FIG. 1 illustrates a wearable device in accordance with implementations of various techniques described herein.

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of fishing and sailing activity detection described herein will now be described in more detail with reference to FIGS. 1-7.

Fishing Activity Detection

Fishermen often record details of their fishing trips so that the information can be referenced at a later time, and so that the trip can be analyzed. Accordingly, various implementations described herein are directed to a wearable device that captures motion data and heart rate data, and that automatically determines when a fishing activity has occurred. Fishing data describing the fishing activity could then be recorded by a computer system. In this manner, a digital record of fishing activities and other information could be created without the need for significant user input. Accordingly, FIG. 1 illustrates a wearable device 100 in accordance with various implementations described herein. The wearable device 100 may be worn around the fisherman's arm or wrist.

The wearable device 100 may be made of a combination of plastics and rubbers, or of any other synthetic material. The wearable device 100 may include a housing in the shape of a band. The wearable device 100 may be waterproof. The wearable device 100 may include a clasp, or another mechanism to aid in removal of the wearable device 100 from a user's arm. The wearable device 100 may include buttons 110.

Figure 2:
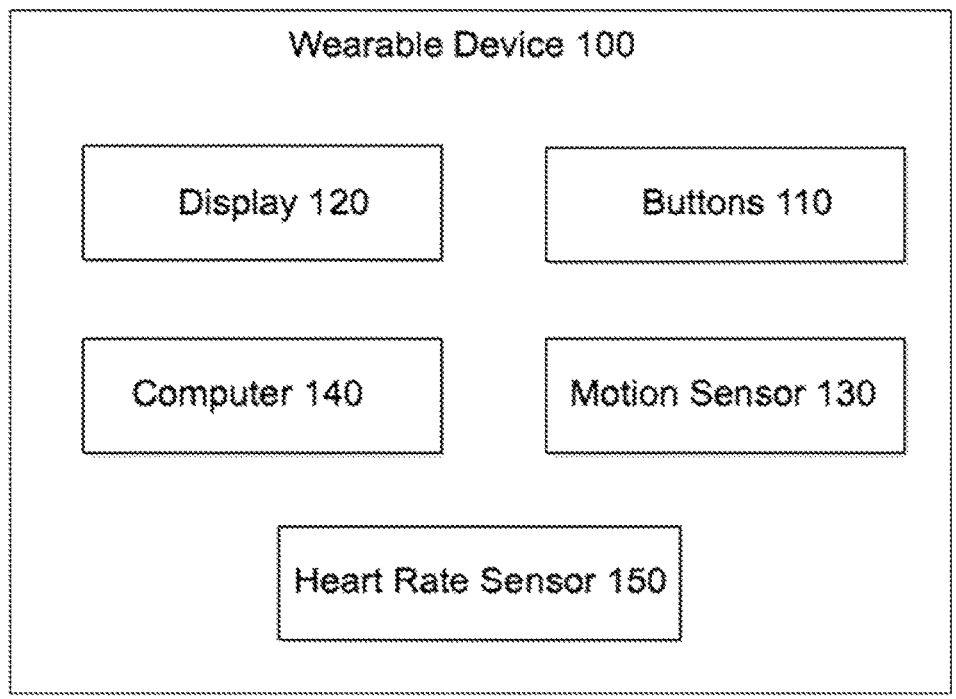
FIG. 2 is a block diagram of a wearable device in accordance with implementations of various techniques described herein.

FIG. 2 is a block diagram of the wearable device 100 in accordance with various implementations described herein. As shown in FIG. 2, the wearable device 100 may include a display 120, buttons 110, at least one motion sensor 130, a computer 140, which is further described in FIG. 6, and a heart rate sensor 150. The at least one motion sensor 130 may include one or more accelerometers, gyroscopes, muscle activity sensors, any other motion sensor, or any combination of motion sensors. The at least one motion sensor 130 is configured to capture motion data.

The heart rate sensor 150 may be located in the wearable device 100, or may communicate wirelessly with the wearable device 100. The heart rate sensor 150 may measure a user's pulse to determine heart rate. The heart rate sensor 150 may be any sensor capable of measuring heart rate or pulse. In one implementation, the heart rate sensor 150 may be an optical sensor used to detect pulse. For example, an optical sensor may be located on a wearable device 100 so that the optical sensor is in contact with a user's skin. The optical sensor may detect blood flow beneath the user's skin and use this information to determine the user's heart rate.

In another implementation, the heart rate sensor 150 may be an electromagnetic sensor. For example, the electromagnetic sensor may be located on a chest strap. The electromagnetic sensor may communicate wirelessly with the wearable device 100 using Bluetooth, the ANT wireless protocol, or through any other wireless method.

The heart rate sensor 150 may be activated whenever the wearable device 100 is in use. Alternately, the heart rate sensor 150 may be activated only when activity is detected. In one implementation, the motion sensor 130 may detect a threshold level of activity, and then the heart rate sensor 150 may be activated in response. In another implementation, the wearable device 100 may only receive or record data from the heart rate sensor 150 when activity is detected. For example, if the heart rate sensor 150 transmits data wirelessly, the wearable device 100 may only receive the data when activity is detected. By activating the heart rate sensor 150 only when activity is detected, the wearable device 100 may consume less electricity and store and process less data.

Figure 6:
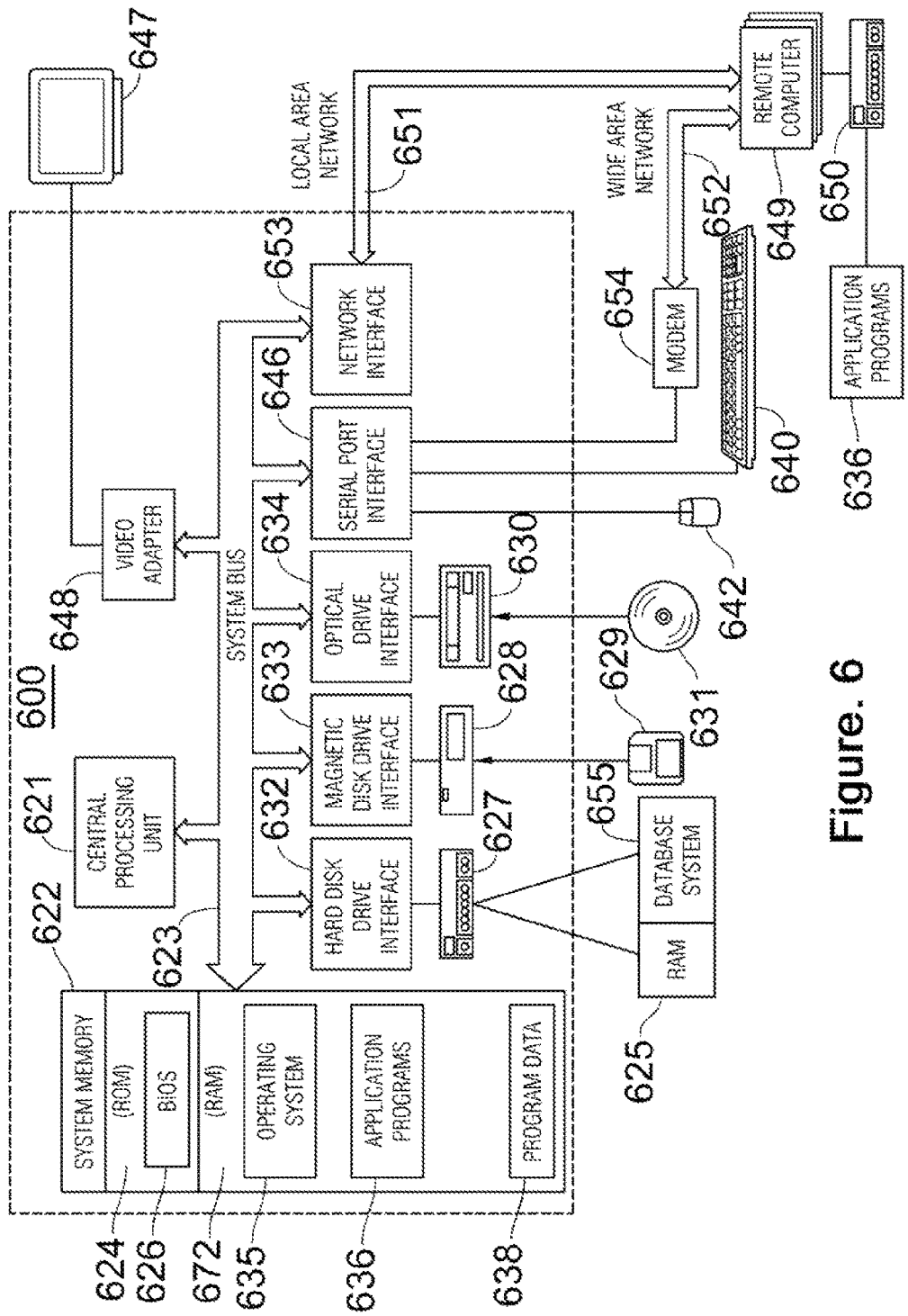
FIG. 6 illustrates a schematic diagram of a computing system in which the various technologies described herein may be incorporated and practiced.

The computer 140 is described in more detail in FIG. 6 In one implementation, the computer 140 may be loaded with software to analyze data from the at least one motion sensor 130 and the heart rate sensor 150. For instance, the software may analyze motion data and heart rate data to determine when a fishing cast motion has been made, and may also determine what type of cast was made. The software may also record that a cast has been made, the time of the cast, e.g., a timestamp, and the type of cast. The software is described in more detail in FIG. 3.

Continuing with describing FIG. 2, the wearable device 100 may include one or more buttons 110. The one or more buttons 110 may be used for user input. For example, the one or more buttons 110 may be used to input the occurrence of a catch.

The wearable device may contain a display 120. The display may be a series of Light Emitting Diodes (LED). The display 120 may be a Liquid Crystal Display (LCD). The display 120 may be used to display a measure of physical exertion, illustrated in FIG. 5. The display 120 may also be used to display any other data recorded using a motion sensor 130 and heart rate sensor 150.

The wearable device 100 may include wireless technology, such as Bluetooth, Wi-Fi, cellular technology such as GSM or CDMA, satellite communication, or any other wireless technology. In one implementation, the wearable device 100 may be connected wirelessly to a marine electronics device 700, which is described in more detail in FIG. 7. Although the wearable device 100 is described as being wirelessly connected to a marine electronics device 700, it should be understood that the wearable device 100 may be connected to any computer system 600, including a portable computer system, a smart phone device, a remote server, a cloud server and the like. It should also be understood that the wearable device 100 may be connected to any other device able to store fishing data, e.g., a data logging device, which may be connected to a marine electronics device 700.

The marine electronics device 700 or a computer system 600, including a smart phone, may record additional data, such as location, speed, weather, or other data. The data from the marine electronics device 700 or computer system 600 and the wearable device 100 may then be combined to provide comprehensive data regarding a fishing trip. The combined data may then be transmitted to a remote server or cloud. In one implementation, the combined data may be transmitted to a smart phone device, which then transmits the data to a remote server or cloud. In another implementation, the combined data may be transmitted to the data logging device, which may then transmit the combined data at a later time. In yet another implementation, the data from the wearable device 100 may be transmitted to the remote server or cloud via the smart phone without using the marine electronics device 700. In still another implementation, the data from the wearable device may be transmitted to a data logging device prior to being transmitted to a remote server or cloud via the smart phone.

Fishing Activity Detection Software

Figure 3:
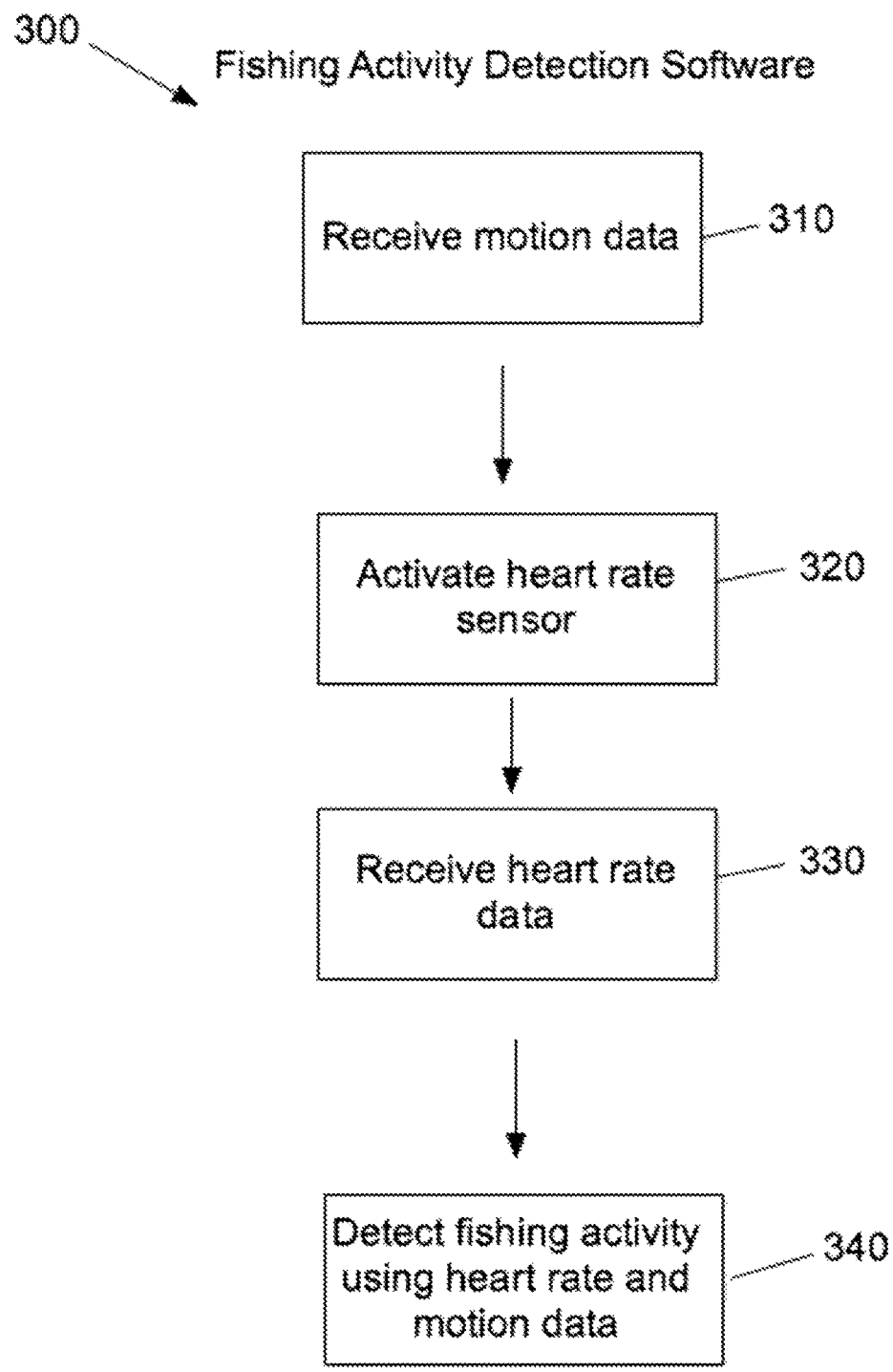
FIG. 3 illustrates a flow diagram describing the operation of a fishing activity detection software in accordance with implementations of various techniques described herein.

FIG. 3 illustrates a flow diagram describing the operation of a fishing activity detection software 300 in accordance with implementations of various techniques described herein. In one implementation, method 300 may be performed by the computer 140. It should be understood that while method 300 indicates a particular order of execution of operations, in some implementations, certain portions of the operations might be executed in a different order. Further, in some implementations, additional operations or steps may be added to the method 300. Likewise, some operations or steps may be omitted.

As mentioned above, the computer 130 contained in a wearable device 100 may be loaded with a set of instructions (software) to analyze data received from one or more sensors. At block 310, the fishing activity detection software 300 may receive motion data from the at least one motion sensor 130 in the wearable device. The software may analyze the motion data to detect activity. If a threshold amount of activity is detected, the software may activate the heart rate sensor 150 at block 320. In one implementation, the motion sensor 130 is recording data throughout a fishing trip, and the heart rate sensor 150 is only recording data when activity is detected by the motion sensor 130. In a second implementation, both the motion sensor 130 and the heart rate sensor 150 record data throughout a fishing trip. In this second implementation, block 320 is skipped. In both implementations, blocks 310 and 330 may operate simultaneously. For example, the software may receive motion data and heart rate data simultaneously.

At block 330, the software may receive heart rate data from the heart rate sensor 150. The heart rate data may consist of a user's pulse. The heart rate data may be measured in beats per minute (BPM), or any other heart rate measurement. For example the heart rate data may consist of a transmission each time a heart beat is detected. In another example, the heart rate data may consist of the current BPM and may be transmitted every tenth of a second. Any data relating to heart rate, heartbeat, or pulse may be received.

At block 340, the software may analyze the motion data and the corresponding heart rate data to determine whether a fishing activity has occurred. The software may also determine what type of fishing activity has occurred. The fishing activity may be a catch, cast, bite, or any other fishing activity. The software may record the occurrence of the fishing activity and the time, e.g., a timestamp in memory inside the computer 130, of the activity. The record may be a database, a log, or any other method of recording the fishing data. The fishing activity may be shown on a display 150. For example, a count of casts may be displayed, or a count of bites. The software may also record a measure of physical exertion corresponding to the fishing activity, as described in FIG. 4.

Fishing activity may be detected at block 340 using motion data, heart rate data, or both. Using both heart rate data and motion data to detect fishing activity may be more precise than using one type of data. Fishing activities, including making a cast or catch, may cause a fisherman's heart rate to increase due to physical exertion. For example, a motion sensor 130 may detect motion that appears to correspond to a catch, and data from the heart rate sensor 150 may indicate an increase in heart rate, confirming the occurrence of the catch. In a second example, the heart rate sensor 150 may detect a change in a user's heart rate, indicating that the user is engaged in a physical activity, and the motion sensor data may be used to determine what fishing activity occurred. In a third example, the software may analyze both heart rate data and motion data simultaneously to detect a fishing activity.

When the trip is over, the software may transmit the recorded data wirelessly to the connected device, e.g., the marine electronics device 700. For example, the recorded data may be a database of detected fishing activities and timestamps for those activities. In another example, the recorded data may include both motion data and heart rate data. In one implementation, the software may transmit the recorded data after each new entry, or at any other interval. For example, the transmission may be made after each cast. The transmission may be to a remote server or to any computer system, including a smart phone or a marine electronics device.

Exertion Monitoring Software

Figure 4:
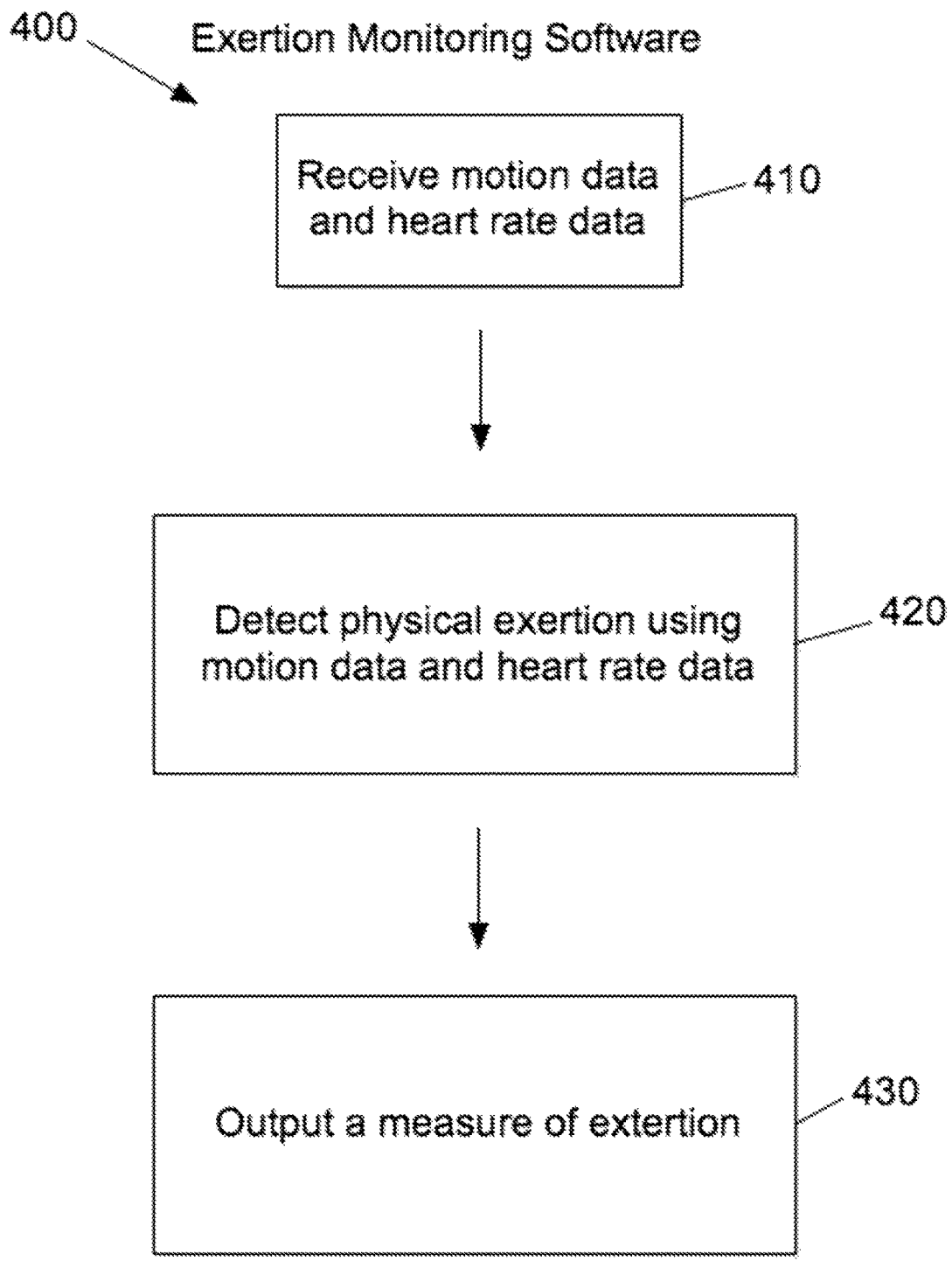
FIG. 4 illustrates a flow diagram describing the operation of an exertion monitoring software in accordance with implementations of various techniques described herein.

FIG. 4 illustrates a flow diagram describing the operation of an exertion monitoring software 400 in accordance with implementations of various techniques described herein. In one implementation, method 400 may be performed by the computer 140. It should be understood that while method 400 indicates a particular order of execution of operations, in some implementations, certain portions of the operations might be executed in a different order. Further, in some implementations, additional operations or steps may be added to the method 400. Likewise, some operations or steps may be omitted.

As mentioned above, the computer 140 contained in a wearable device 100 may be loaded with a set of instructions (software) to analyze data received from one or more sensors. At block 410, the exertion monitoring software 400 may receive motion data, heart rate data, or both. The received data may be recorded using a wearable device 100 during a fishing trip or a sailing trip.

At block 420, the software may detect physical exertion using the received motion data, heart rate data, or both. The physical exertion may correspond to a user's activities during a fishing trip or while sailing. For example, while fishing a user may be particularly active during a fishing catch, particularly during the fight portion of a catch. In another example, while sailing, a user may be particularly active during a turn (i.e. a tack), or while operating a winch. These activities may result in an increased heart rate, and increase in motion. These increases may be reflected in the data captured by the heart rate and motion sensors. The software may process the sensor data to determine the level of exertion.

The level of exertion detected at block 420 may be determined using motion data, heart rate data, or both. For example, the software may examine the amount of increase in heart rate and the length of time that heart rate is increased. In another example, the software may examine the amount of motion detected and the length of time that motion is detected.

At block 430, the software may output a measure of the physical exertion. The measure may be an estimate of calories burned, a numeral describing the level of physical exertion, or any other indicator of physical exertion. In one implementation, the numeral may range from 1, corresponding to low exertion, to 10, corresponding to high exertion. For example, a fishing catch with a routine two minute fight may have a rating of 2, while a catch with a vigorous forty minute fight may have a rating of 8. Although the numeral is described as ranging from 1 to 10, the numeral may have any range. Additionally, any other type of indicator may be used to display the level of exertion, for example, a symbol or a chart. Examples of output are further described in FIG. 5.

The exertion monitoring software 400 may be used to measure fishing activities, such as casts, catches, fights during a catch, or any other fishing activity. The exertion monitoring software 400 may also be used to measure physical exertion during other activities, including sailing activities. For example, in a sailing trip, the exertion monitoring software 400 may be used to measure the exertion while tacking or during any other activity, or throughout an entire race or sailing trip.

The physical exertion level during a fishing activity or trip, or sailing activity or trip may be automatically recorded. The physical exertion level may be used in a competition. For example, multiple fishermen on a fishing trip may engage in a competition to determine which fishermen had the highest exertion level during a single fishing catch.

Physical Exertion Display

Figure 5:
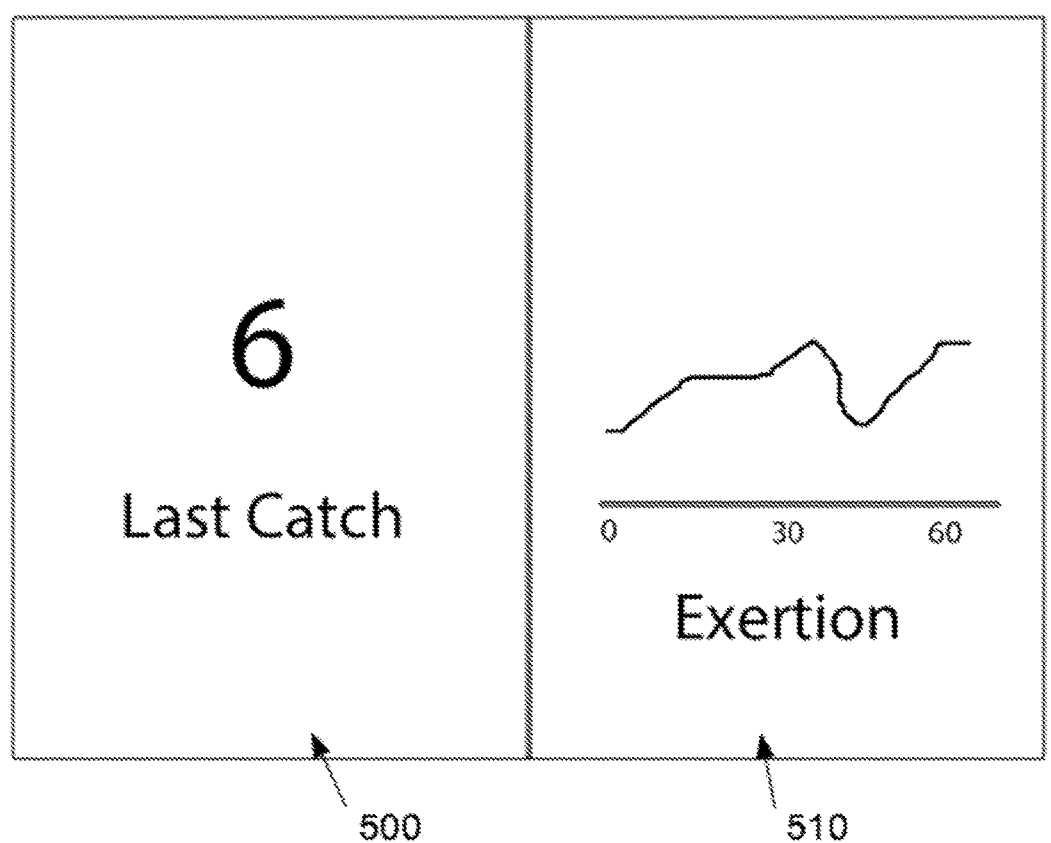
FIG. 5 illustrates physical exertion displays in accordance with implementations of various techniques described herein.

FIG. 5 illustrates physical exertion displays 500 and 510 in accordance with implementations of various techniques described herein. The physical exertion displays 500 and 510 may be displayed on a marine electronics device 700, computer system 600, wearable device 100, smartphone, or any other device. Physical exertion displays 500 and 510 may display data determined using exertion monitoring software 400.

The level of physical exertion measured during fishing activities or while sailing may be displayed during an activity, immediately following an activity, or may be stored for later viewing. Additionally, a graph may be generated to display the level of exertion over time. In physical exertion display 500, a numeral is used to represent the exertion level measured during the last fishing catch. This type of display could also be used to represent the exertion level measured during the last tack in a sailing trip, or during any other fishing or sailing activity. Additionally, the display could represent the exertion level over a longer period of time, for example, an entire sailing trip or fishing trip.

Physical exertion display 510 shows a graph of exertion over a 60 minute time period. Although the period is shown as 60 minutes, any time period may be used. Although FIG. 5 illustrates two examples of displays for physical exertion during a fishing trip or while sailing, any other type of display may be used to show the physical exertion data.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may also be implemented in distributed computing environments where tasks are performed by remote processing devices that are linked through a communications network, e.g., by hardwired links, wireless links, or combinations thereof. In a distributed computing environment, program modules may be located in both local and remote computer storage media including memory storage devices.

FIG. 6 illustrates a computer system 600 into which implementations of various technologies and techniques described herein may be implemented. Computing system 600 may be a conventional desktop, a handheld device, a wearable device, a controller, a personal digital assistant, a smart phone, a server computer, an electronic device/instrument, a laptop, a tablet, or part of a navigation system, marine electronics, or sonar system. It should be noted, however, that other computer system configurations may be used.

The computing system 600 may include a central processing unit (CPU) 621, a system memory 622 and a system bus 623 that couples various system components including the system memory 622 to the CPU 621. Although only one CPU is illustrated in FIG. 6, it should be understood that in some implementations the computing system 600 may include more than one CPU. The system bus 623 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 622 may include a read only memory (ROM) 624 and a random access memory (RAM) 625. A basic input/output system (BIOS) 626, containing the basic routines that help transfer information between elements within the computing system 600, such as during start-up, may be stored in the ROM 624. The computing system may be implemented using a printed circuit board containing various components including processing units, data storage memory, and connectors.

The computing system 600 may further include a hard disk drive 627 for reading from and writing to a hard disk, a magnetic disk drive 628 for reading from and writing to a removable magnetic disk 629, and an optical disk drive 630 for reading from and writing to a removable optical disk 631, such as a CD ROM or other optical media. The hard disk drive 627, the magnetic disk drive 628, and the optical disk drive 630 may be connected to the system bus 623 by a hard disk drive interface 632, a magnetic disk drive interface 633, and an optical drive interface 634, respectively. The drives and their associated computer-readable media may provide nonvolatile storage of computer-readable instructions, data structures, program modules and other data for the computing system 600.

Although the computing system 600 is described herein as having a hard disk, a removable magnetic disk 629 and a removable optical disk 631, it should be appreciated by those skilled in the art that the computing system 600 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 600. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on the hard disk 627, magnetic disk 629, optical disk 631, ROM 624 or RAM 625, including an operating system 635, one or more application programs 636, program data 638, and a database system 655. The one or more application programs 636 may contain program instructions configured to perform methods 300 and 400 according to various implementations described herein. The operating system 635 may be any suitable operating system that may control the operation of a networked personal or server computer, such as Windows® XP, Mac OS® X, Unix-variants (e.g., Linux® and BSD®), and the like.

A user may enter commands and information into the computing system 600 through input devices such as a keyboard 640 and pointing device 642. Other input devices may include a microphone, joystick, game pad, satellite dish, scanner, user input button, or the like. These and other input devices may be connected to the CPU 621 through a serial port interface 646 coupled to system bus 623, but may be connected by other interfaces, such as a parallel port, game port or a universal serial bus (USB). A monitor 647 or other type of display device may also be connected to system bus 623 via an interface, such as a video adapter 648. In addition to the monitor 647, the computing system 600 may further include other peripheral output devices such as speakers and printers.

Further, the computing system 600 may operate in a networked environment using logical connections to one or more remote computers 649. The logical connections may be any connection that is commonplace in offices, enterprise-wide computer networks, intranets, and the Internet, such as local area network (LAN) 651 and a wide area network (WAN) 652. The remote computers 649 may each include application programs 636 similar to that as described above. The computing system 600 may use a Bluetooth radio to wirelessly communicate with another device.

When using a LAN networking environment, the computing system 600 may be connected to the local network 651 through a network interface or adapter 653. When used in a WAN networking environment, the computing system 600 may include a modem 654, wireless router or other means for establishing communication over a wide area network 652, such as the Internet. The modem 654, which may be internal or external, may be connected to the system bus 623 via the serial port interface 646. In a networked environment, program modules depicted relative to the computing system 600, or portions thereof, may be stored in a remote memory storage device 650. It will be appreciated that the network connections shown are exemplary and other means of establishing a communications link between the computers may be used.

Marine Electronics Device

Figure 7:
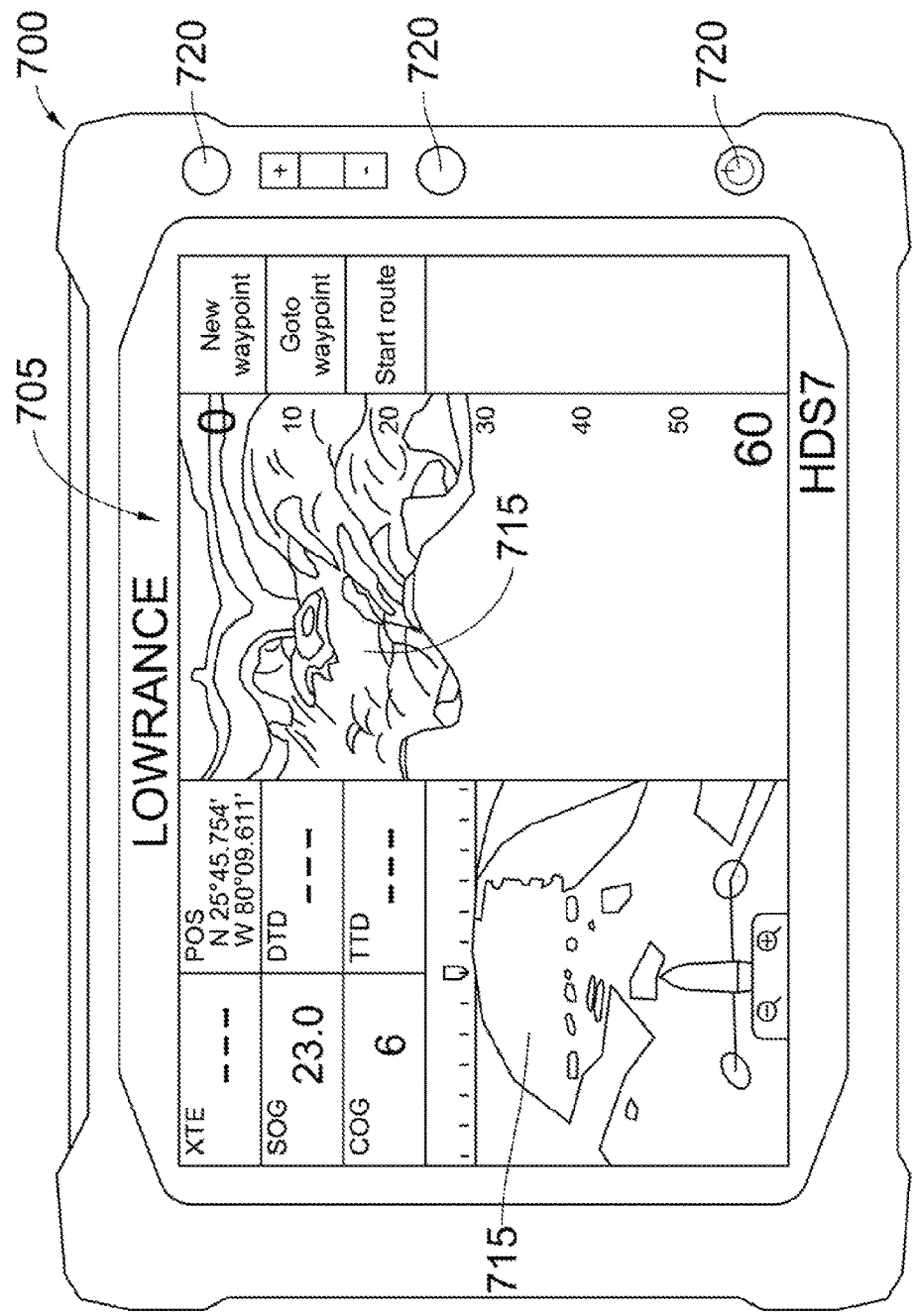
FIG. 7 illustrates a schematic of a marine electronics device in accordance with implementations of various techniques described herein.

FIG. 7 illustrates a schematic diagram of a marine electronics device 700 in accordance with various implementations described herein. The marine electronics device 700 includes a screen 705. In certain implementations, the screen 705 may be sensitive to touching by a finger. In other implementations, the screen 705 may be sensitive to the body heat from the finger, a stylus, or responsive to a mouse. The display device 700 may display marine electronic data 715. The marine electronic data types 715 may include chart data, radar data, sonar data, steering data, dashboard data, navigation data, fishing activity information detected using fishing activity detection software 300, physical exertion information from exertion monitoring software 400 and the like. The marine electronics device 700 may also include a plurality of buttons 720, which may be either physical buttons or virtual buttons, or a combination thereof. The contents of the marine display device 700 are described in more detail with reference to FIG. 6.

While the foregoing is directed to implementations of various techniques described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims

What is claimed is:

1. A wearable device for determining fishing activity, the wearable device comprising:
   a housing;
   a heart rate sensor within the housing;
   a motion sensor within the housing; and
   a computer system having a processor and memory, wherein the processor is within the housing and operably coupled to the heart rate sensor and the motion sensor, wherein the memory has stored thereon a plurality of executable instructions which, when executed by the processor, cause the processor to:
      measure motion data from the motion sensor, wherein the motion data corresponds to movement of a user of the wearable device;
      measure, via the heart rate sensor, a pulse of the user of the wearable device;
      determine heart rate data from the pulse of the user measured by the heart rate sensor;
      determine, based on a received combination of the motion data and the heart rate data, a type of a fishing activity that occurred, wherein the determined type of fishing activity comprises one of a cast, a catch, or a bite, wherein the detected motion data and the determined heart rate data each correspond to the determined type of fishing activity that occurred; and
      store fishing activity data in a memory.

2. The wearable device of claim 1, wherein the memory further comprises executable instructions which, when executed by the processor, cause the processor to record that the fishing activity has occurred and a timestamp corresponding to the fishing activity.

3. The wearable device of claim 1, wherein the wearable device further comprises a display for displaying information pertaining to the fishing activity.

4. The wearable device of claim 1, wherein the motion sensor is an accelerometer.

5. A non-transitory computer-readable medium having stored thereon a plurality of computer-executable instructions which, when executed by a computer, cause the computer to:
   measure motion data from a first sensor located within a housing of a wearable device configured to determine fishing activity, wherein the motion data corresponds to movement of a user of the wearable device;
   in response to determining an instance in which the received motion data satisfies an activity threshold:
      activate a second sensor located within the housing of the wearable device, wherein the computer is within the housing and operably coupled to both the first sensor and the second sensor; and
      measure a pulse of the user of the wearable device using the second sensor;
   determine heart rate data from the pulse of the user measured by the second sensor;
   analyze the motion data and the heart rate data together;
   determine whether the received combination of motion data and heart rate data correspond to a fishing activity; and
   store fishing activity data in a memory.

6. The non-transitory computer-readable medium of claim 5, wherein the instructions further cause the computer to record that the fishing activity has occurred and a timestamp corresponding to the fishing activity.

7. The non-transitory computer-readable medium of claim 5, wherein the instructions further cause the computer to determine the level of physical exertion corresponding to the fishing activity.

8. The non-transitory computer-readable medium of claim 7, wherein the instructions further cause the computer to determine a numeral corresponding to the level of physical exertion.

9. A wearable device for determining fishing activity, the wearable device comprising:
   a housing;
   a heart rate sensor located within the housing;
   a motion sensor located within the housing; and
   a computer system having a processor and memory, wherein the processor is within the housing and operably coupled to the heart rate sensor and the motion sensor, wherein the memory has stored thereon a plurality of executable instructions which, when executed by the processor, cause the processor to:
      measure motion data from the motion sensor, wherein the motion data corresponds to movement of a user of the wearable device;
      measure, via the heart rate sensor, a pulse of the user of the wearable device;
      determine heart rate data from the pulse of the user measured by the heart rate sensor;
      determine, based on a received combination of the motion data and the heart rate data, a type of fishing activity that occurred, wherein the determined type of fishing activity comprises one of a cast, a catch, or a bite, wherein the detected motion data and the determined heart rate data each correspond to the determined type of fishing activity that occurred;
      determine a level of physical exertion based on the combination of the motion data and the heart rate data, wherein the level of physical exertion corresponds to the determined type of fishing activity that occurred; and
      store fishing activity data in a memory.

10. The wearable device of claim 9, wherein the memory further comprises executable instructions which, when executed by the processor, cause the processor to record the level of physical exertion as a numeral corresponding to the level of exertion.

11. The wearable device of claim 9, wherein the memory further comprises executable instructions which, when executed by the processor, cause the processor to record the level of physical exertion as a number of calories.

12. The wearable device of claim 9, wherein the determined level of physical exertion is used to determine a winner of a competition.

13. The wearable device of claim 9, wherein the wearable device further comprises a display, and the determined level of physical exertion is shown on the display.

14. The wearable device of claim 1, wherein the heart rate sensor is an optical sensor or an electromagnetic sensor.

15. The non-transitory computer-readable medium of claim 5, wherein the second sensor is an optical sensor or an electromagnetic sensor.

16. The wearable device of claim 1, wherein the memory further comprises executable instructions which, when executed by the processor, cause the processor to determine the type of the fishing activity by:

determining an instance in which the received motion data satisfies an activity threshold; and in response:
activating the heart rate sensor to measure the pulse of the user; and
determining whether the fishing activity occurred using the determined heart rate data.

17. The wearable device of claim 1, wherein the memory further comprises executable instructions which, when executed by the processor, cause the processor to determine the type of the fishing activity by:

determining whether the received heart rate data indicates that the user is engaged in a physical activity, and
determining whether the physical activity corresponds to the fishing activity using the received motion data.

18. The wearable device of claim 1, wherein the memory further comprises executable instructions which, when executed by the processor, cause the processor to determine the type of the fishing activity by simultaneously analyzing the received motion and heart rate data.

* * * * *